United States Patent
Phee Soo Jay et al.

(10) Patent No.: US 6,939,291 B2
(45) Date of Patent: Sep. 6, 2005

(54) ENDOSCOPIC DEVICE FOR LOCOMOTION THROUGH THE GASTRO-INTESTINAL TRACT

(75) Inventors: Louis Phee Soo Jay, Singapore (SG); Alberto Arena, Messina (IT); Arianna Menciassi, Pontedera (IT); Paolo Dario, Livorno (IT)

(73) Assignee: Korea Institute of Science and Technology (KR)

(*) Notice: Subject to any disclaimer, the term of this patent is extended or adjusted under 35 U.S.C. 154(b) by 121 days.

(21) Appl. No.: 10/469,340

(22) PCT Filed: Feb. 28, 2001

(86) PCT No.: PCT/KR01/00304

§ 371 (c)(1),
(2), (4) Date: Aug. 27, 2003

(87) PCT Pub. No.: WO02/068035

PCT Pub. Date: Sep. 6, 2002

(65) Prior Publication Data

US 2004/0073082 A1 Apr. 15, 2004

(51) Int. Cl.⁷ ................................................ A61B 1/04
(52) U.S. Cl. .................................... 600/114; 604/95.03
(58) Field of Search ........................ 600/114–116, 101, 600/156, 159; 128/897, 899; 604/95.01–95.04, 96.01, 97.01

(56) References Cited

U.S. PATENT DOCUMENTS

| | | | |
|---|---|---|---|
| 4,176,662 A | * 12/1979 | Frazer | .................... 600/114 |
| 4,389,208 A | 6/1983 | LeVeen et al. | |
| 5,364,353 A | 11/1994 | Corfitsen et al. | |
| 5,398,670 A | 3/1995 | Ortiz et al. | |
| 5,662,587 A | * 9/1997 | Grundfest et al. | .......... 600/114 |
| 5,906,591 A | 5/1999 | Dario et al. | |
| 6,007,482 A | * 12/1999 | Madni et al. | ................ 600/115 |
| 6,764,441 B2 | * 7/2004 | Chiel et al. | .................. 600/115 |

* cited by examiner

*Primary Examiner*—John P. Lacyk
(74) *Attorney, Agent, or Firm*—Ostrolenk, Faber, Gerb & Soffen, LLP

(57) ABSTRACT

An endoscopic device for locomotion in a body cavity according to a prefixed advancing direction (A) comprising at least a variable length intermediate section (1a, 21a) extending between a front end section (1b, 21b) and a rear end section (1c, 21c). First and second clamping means (7, 12, 27, 32) are integral to the front and rear section, for alternately grasping respective surrounding portions of wall (P) of the body cavity. Sucking means (13, 14, 37, 38) are associated to the first and second clamping means for creating a depression sufficient to cause the body cavity wall portions to collapse within the first and second clamping means while they are in an open condition. Means for actuating alternate extensions and retractions of the intermediate section and actuating means (6, 11, 26, 31) of the first and second clamping means are further provides for synchronous operation to generate a forward motion of the rear end section due to a retraction of the intermediate section, the wall portion (P) surrounding the first clamping means being firmly held therebetween, and to generate a forward motion of the front end section due to an extension of the intermediate section, the wall portion (P) surrounding the second clamping means being firmly held therebetween.

24 Claims, 6 Drawing Sheets

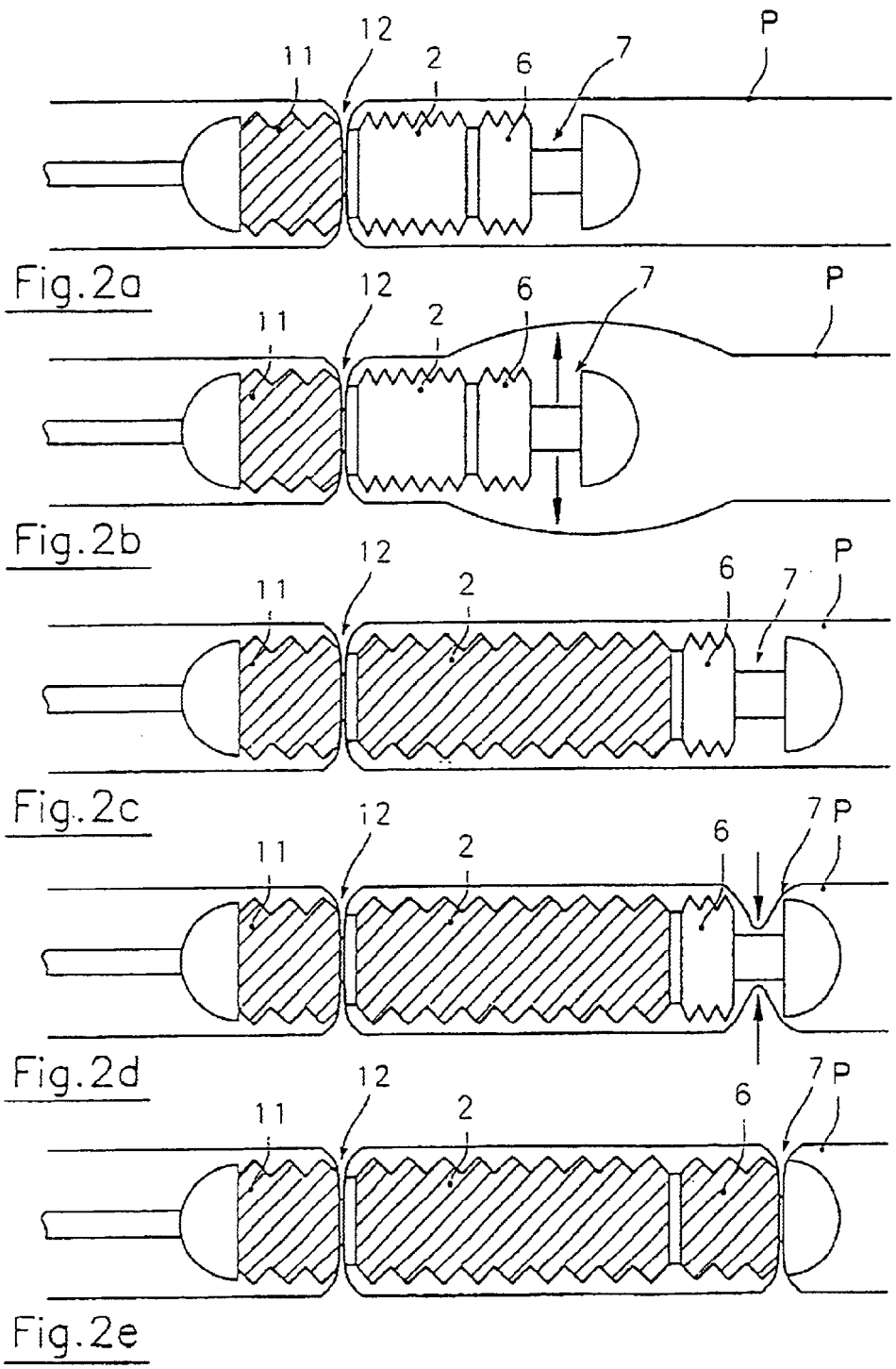

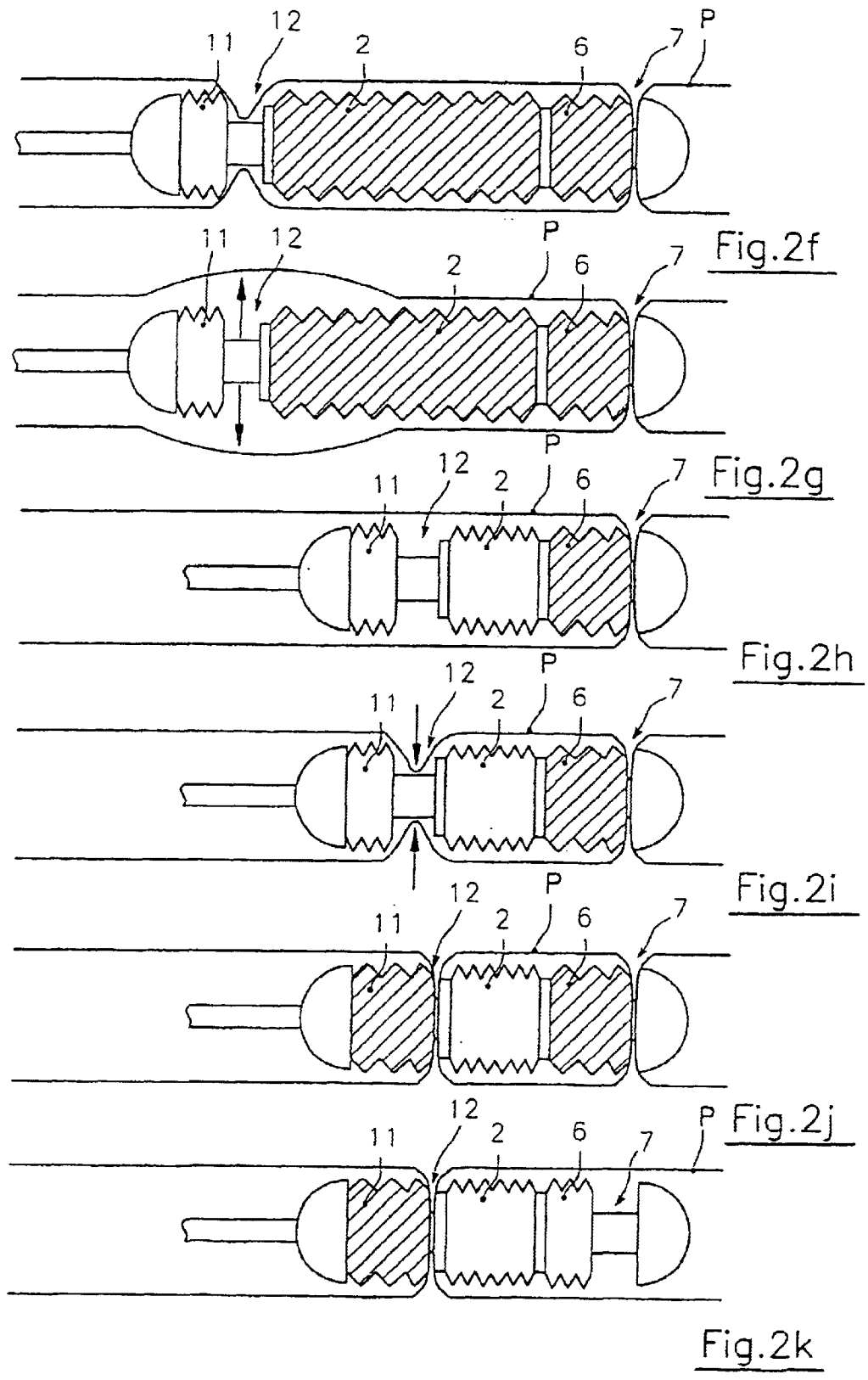

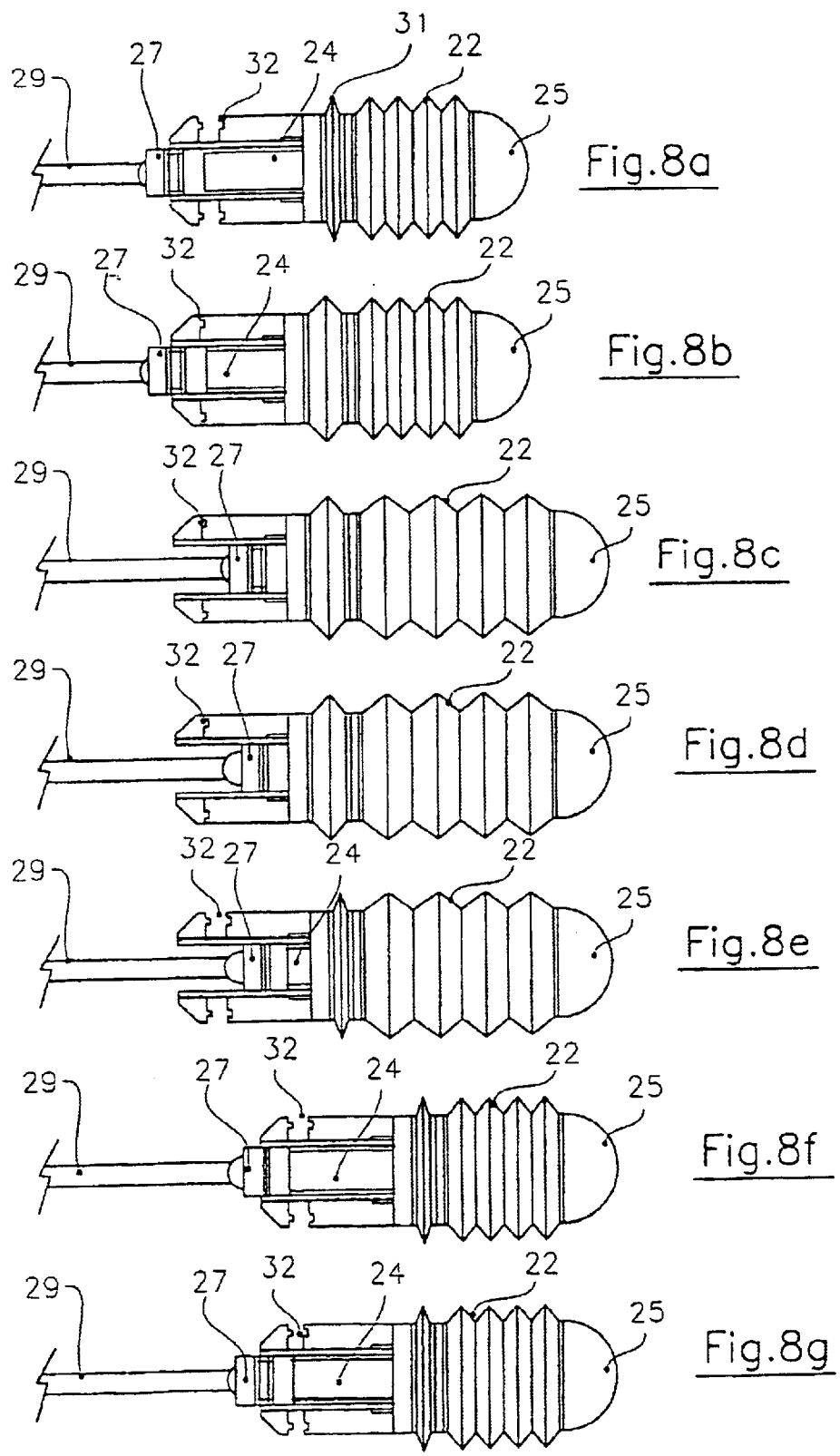

ENDOSCOPIC DEVICE FOR LOCOMOTION THROUGH THE GASTRO-INTESTINAL TRACT

FIELD OF THE INVENTION

The present invention relates to an endoscopic device for locomotion through a tubular body cavity, in particular, but not exclusively, through the gastrointestinal tract, able to migrate in a prefixed direction with so-called inchworm motion.

BACKGROUND OF THE INVENTION

Endoscopic devices for surgical or diagnostic procedure are already known. These devices are operated by the surgeon who directly imparts to the device the forward motion through the patient's body. Surgical and/or diagnostic instruments which are necessary to carry out each specific procedure, such as microarms, microcameras, and/or laser emitters are generally associated to these devices.

In order to make easier the surgeon's task there have been proposed endoscopic devices of the above mentioned type capable of a semi-autonomous movement within the body cavity of a patient, adapting their shape, as far as possible, to the shape of the surrounding cavity. In this case, the walls of the body cavity act as a support for propelling the device forward. For example, in U.S. Pat. No. 5,398,670 there is disclosed an endoscopic instrument substantially formed by a bellows-shaped tubular body, capable of extension and retraction, and by two end portions including respective inflatable balloon members, by means of which the front end portion and the rear end portion alternately engage by compression with the walls of the body cavity through which the device must be pushed forward. There is provision for a control system which operates the inflation and deflation of the two balloon members and the extension and retraction of the tubular body according to a sequence such as to produce the advancement of the device in the prefixed direction.

An endoscopic device of the same type is disclosed in U.S. Pat. No. 5,906,591, in which, however, a vacuum pressure sufficient to produce, under the induced sucking conditions, a substantial anchorage of the front and rear end portions to the cavity wall is created sequentially around these end portions.

When the endoscopic device of the type described in the above cited patents is destined to the locomotion through the gastro-intestinal tract, its anchorage to the cavity walls is not satisfactory, because this type of cavity is soft, slippery and often wet. Using balloon-type endoscopic devices such that according to U.S. Pat. No. 5,298,670, even if the intestinal wall is overextended, it is impossible to produce sufficient traction forces due to extremely low friction coefficient of the gastrointestinal tract. Furtheremore, excessive overextension of the balloon will result in causing severe pain for the patient. A similar result is obtained by increasing the suction in the case of the endoscopic device of U.S. Pat. No. 5,906,591, with the drawback that, when the degree of vacuum is increased over a certain extent, undesirable lesions may appear.

In order to improve the anchorage of the endoscopic devices of the above mentioned type it has proposed to equip them with auxiliary anchoring means of various shapes, which, however, increase the structural complexity and the length of the device and increase the patient discomfort and the risk of damage of the involved tissues.

SUMMARY OF THE INVENTION

The object of the present invention is to provide an endoscopic device of the semi-autonomous locomotion type through a body cavity such as the gastro-intestinal tract, capable of assuring a suitable anchorage to the body cavity thereby allowing its advancement through it, without giving rise to any of the problems encountered with the similar known devices.

Another object of the present invention is to provide an endoscopic device of the above mentioned type for achieving a suitable anchorage to the cavity wall by means of structurally simple solutions allowing the size of the device to be kept small.

These object are reached with the endoscopic device for locomotion in a body cavity in a prefixed advancement direction according to the present invention, comprising at least a variable length intermediate section extending between a front end section and a rear end section with respect to said direction and first and second clamping means integral to the front end section and, respectively, the rear end section, for selectively grasping respective surrounding portions of the wall of the body cavity. Associated to the first and second clamping means suction means are provided for creating a vacuum sufficient to cause the surrounding portions of the body cavity walls to collapse within the first and the second clamping means, when they are in their open condition, to allow a firm grasping when said clamping means are closed. Means For operating alternate elongations and retractions of the intermediate section and means for operating the first and second clamping means, synchronously operated to cause an advancement of the rear end section device in the prefixed direction following a retraction of the intermediate section when the respective portion of surrounding wall is firmly engaged with the first clamping means, and to cause an advancement of the front end section in the same direction following an elongation of the intermediate section when the respective surrounding wall portion is firmly engaged within the second clamping means.

Furthermore, the present invention provides a method for producing the locomotion through body cavities of an endoscopic device, by means of successive extensions and retractions of at least one variable length intermediate section thereof according a prefixed direction defining front end section and a rear end section of the device, to which first and second clamping means are respectively associated selectively operable from the outside synchronously with the successive extensions and retractions of the intermediate section. The method is characterized by inducing selectively by suction a pneumatic depression in correspondence to one of the first or the second clamping means in their open condition, the depression being such that to cause the surrounding portion of body cavity wall to collapse within said clamping means, and closing said clamping means to grasp said surrounding wall portion and firmly anchoring to it the respective end section to allow the free movement of the other end section in the prefixed direction.

The main advantage of the endoscopic device of the invention consists in that it can migrate through a tubular body cavity in every condition whatever the available friction forces and the compliance of the body cavity are

BRIEF DESCRIPTION OF THE DRAWINGS

Further characteristics and advantages of the endoscopic device according to the invention will become more apparent from the following description of exemplifying, not limiting embodiments thereof, made with reference to the annexed drawings, in which:

FIGS. 2a–2k show and advancement cycle of the device of FIG. 1;

FIGS. 8a–8g show and advancement cycle of the endoscopic device according to FIG. 3.

DESCRIPTION OF THE PREFERRED EMBODIMENT

Figure 1:
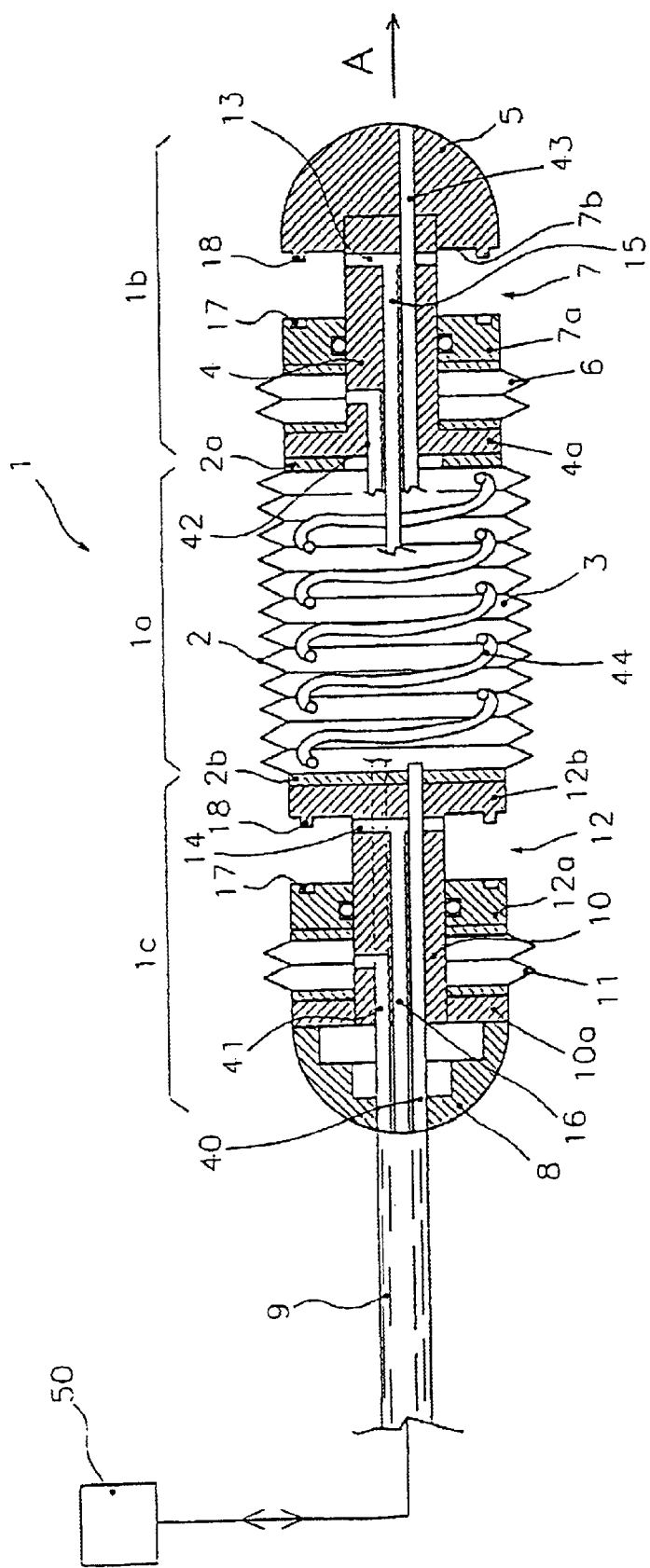
FIG. 1 is a longitudinal sectional view of a first embodiment of the endoscopic device according to the present invention.

With reference to FIG. 1, it has been generally indicated at 1 an endoscopic device according to the present invention. It comprises an intermediate section 1a of a tubular shape, extending between two end sections called front end section 1b and rear end section 1c, the terms "front" and "rear" being referred to a reference direction indicated at A. Clearly, the endoscopic device will be able to move in the body cavity in a forward and a backward direction. The tubular intermediate section 1a is formed by a wall 2 made of elastic and flexible material shaped like a bellows and delimiting a cavity 3 for containing a fluid, for example air. The intermediate section ends with a front flange 2a and a rear flange 2b through which it is connected to front end section 1b and rear end section 1c respectively.

Front end section 1b of the device is formed by a stem 4 fixed to front flange 2a at a flanged end 4a thereof and to a front head 5 of the device at the other end. Fixed to flanged end 4a of stem 4, at the opposite side of flange 2a, is a bellows member 6 which is integral to a jaw 7a of a first clamp 7 (also called front clamp) slidably mounted on stem 4 and fixed to the free end of bellows 6. The other jaw 7b of first clamp 7 is constituted by a face of front head 5 perpendicular to the axis of stem 4 and faced toward first jaw 7a.

Rear end section 1c is formed by a rear head 8, from which a tubular connector 9 extends, connected to a flanged end 10a of a stem 10. Fixed to flanged end 10a, at the opposite side of rear head 8, is a bellows member 11 integral to a jaw 12a of a second clamp 12 (also called rear clamp) coaxially and slidably mounted on stem 10, the other jaw 12b of second clamp 12 being formed by a plate fixed to the end of stem 10 at one side thereof and to rear flange 2b of intermediate section 1a at the other side.

Figure 3:
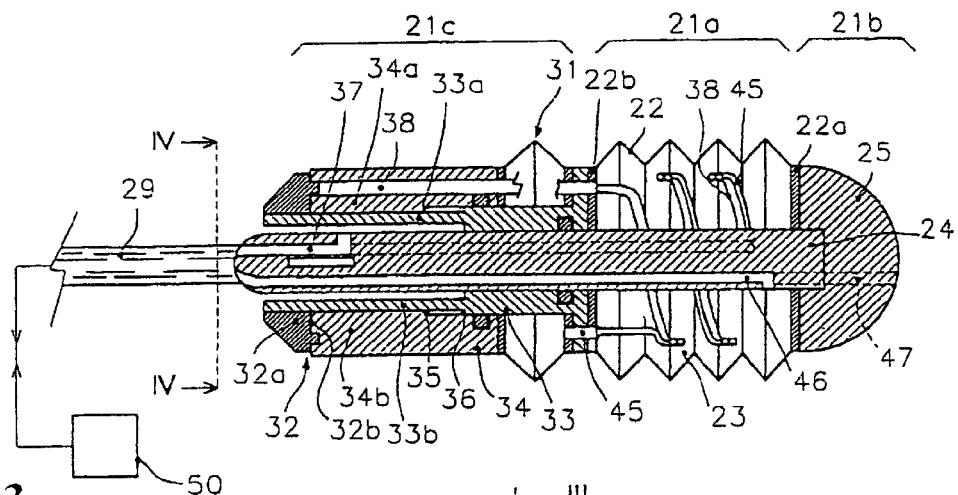
FIG. 3 is a longitudinal sectional view of a second embodiment of the device according to the present invention.

Tubular connector 9 puts into communication the device with an external control system, of the conventional type, for example as described and shown in FIG. 3 of U.S. Pat. No. 5,906,591, comprising a source (50) for selectively providing a positive or negative pressure to the various parts of the devices as will be explained below. More precisely, connector 9 houses pneumatic conduits extending in a substantially axial way within device 1 (as schematically shown in FIG. 1), each of them being able to both feed compressed air to and suck air from chamber 3 of bellows-shaped intermediate section 1a (conduit 40), bellows member 6 and 11 controlling the operation of clamps 7 and 12 (conduits 41, 42), as well as to/from a surface portion of stems 4 and 10 comprised between jaws 7a, 7b and 12a, 12b, respectively, of clamps 7 and 12, through diametral ducts 13 and 14 extending from respective axial ducts 15 and 16 formed in stems 4 and 10, communicating with respective pneumatic conduits housed within connector 9. A further pneumatic conduit. 43 outflows from front head 5 to blow air jets useful to assisting forward motion of the device. In particular, pneumatic conduits passing through intermediate section 1a are helically arranged within chamber 3 as schematically indicated at 44 in FIG. 1.

The operating cycle of the endoscopic device is now described with reference also to FIGS. 2a–2k (the parts being in turn under pressure are shown as hatched). By creating suction conditions at rear clamp 12 a substantially annular portion P of the surrounding wall of the body cavity is caused to collapse between jaws 12a, b which, by adduction of compressed air within bellows 11, close against each other firmly grasping wall portion P (FIG. 2a). Through radial duct 13 of stem 4 air is blown against cavity wall P to cause its displacement from front end section 1b of the device (FIG. 2b). Then compressed air is fed to bellows 2 which elongates pushing front end section 1b of the device forward (FIG. 2c). At this point, a depression is created between jaws 7a, b of front clamp 7 which causes a substantially annular portion of the surrounding cavity wall P to collapse therebetween. By adducting compressed air bellows 6 is caused to elongate and clamp 7 closes firmly grasping cavity wall (FIG. 2e). Bellows 11 is then retracted by depression to open clamp 12 (FIG. 2f) releasing the grasped cavity wall which is displaced back from rear end section 1c of the device by means of air jets through radial duct 14 of stem 10 (FIG. 2g). Rear end section 1c is then pulled forward by bellows 2 which retracts due to depression induced therein (FIG. 2h). At this point, rear clamp 12 grasp a new annular portion of surrounding cavity wall P by creation of a depression between jaws 12a, 12b (FIG. 2i) and closure of rear clamp 12 (FIG. 2j), while front clamp 7 opens to release the grasped annular wall portion. Then the cycle is repeated with a new advancement step.

In order to improve the grip of jaws 7a, 7b and 12a, 12b of front clamp 7 and rear clamp 12 respectively, a circular groove 17 is formed on one of their opposed faces and a corresponding step 18 for engaging with groove 17 is formed on the other face. Advantageously all the edges of the grip surfaces are beveled to avoid any tissue damage.

A second embodiment of the endoscopic device according to the invention is shown in FIGS. 3, 4, 5, 6a –c and 7a, b. In the figures, 21a indicates an intermediate tubular section of the device formed by a bellows wall 22 made of elastic and flexible material delimiting a chamber 23, 21b indicates a front end section connected to intermediate section 21a through a front flange 22a and 21c indicates a rear end section connected to intermediate section 21a through a rear flange 22b.

Figure 7A:
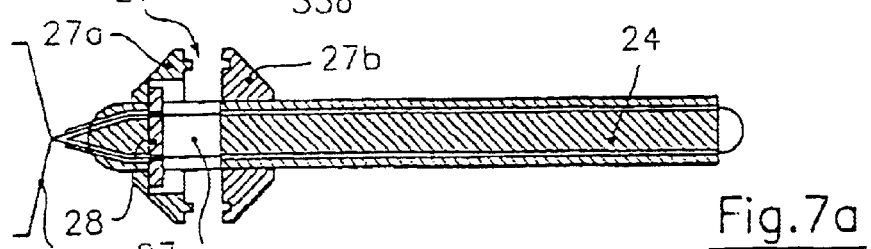
FIGS. 7a, 7b schematically show the operation of the clamping means integral to the front end of the endoscopic device of FIG. 3.
Figure 7B:
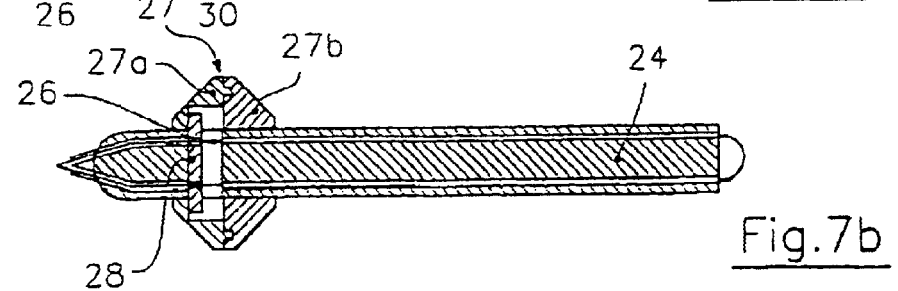

Front end section 21b comprises a head 25 conected to front flange 22a and integral to a stem 24 axially extending through intermediate section 21a and rear end section 21c and connected to a tubular connector 29. A first clamp 27 is mounted at the end of stem 24 opposite to that where head 25 is fixed. Each clamp is formed by a jaw 27a axially slidable on stem 24 and by a jaw 27b fixedly connected thereto. Jaw 27*a* and 27*b* are each formed by a pair of jaw portions diametrically arranged on stem 24. The two portions of jaw 27*a* are mutually connected by means of a bracket 28 passing through a slot 30 diametrically formed in stem 24. An actuating wire 26 crosses bracket 28 in two points and is fixed to the bracket at one of them while being slidable at the other one. Wire 26 slidably extends through the overall length of stem 24 forming a loop along it and its free ends are conveyed externally through connector 29. Clearly, by pulling one of the two ends from the outside, the opening and closure of clamp 27 can be controlled, as also shown in FIGS. 7*a* and 7*b*.

Figure 4:
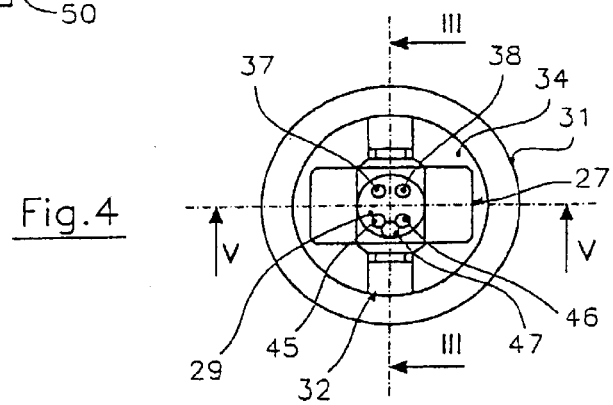
FIG. 4 is a cross sectional view of the endoscopic device of FIG. 3 taken along arrows IV—IV.
Figure 5:
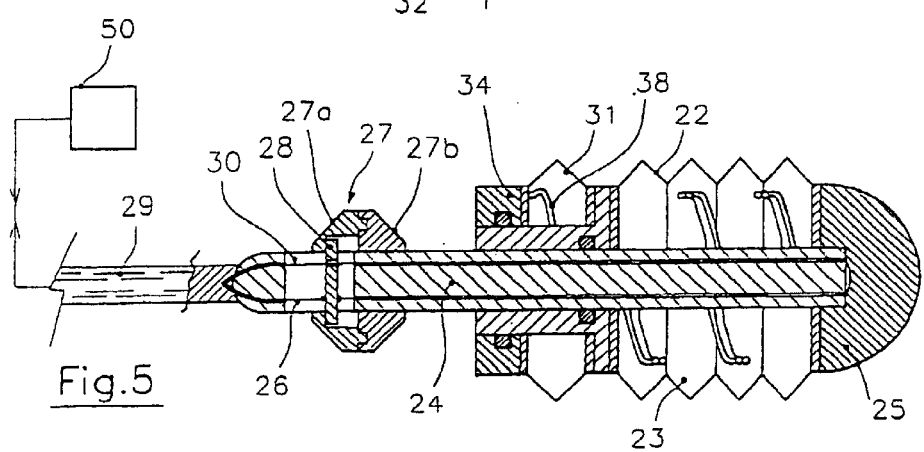
FIG. 5 is a longitudinal sectional view of the endoscopic device of FIG. 3 taken along arrows V—V of FIG. 4.
Figure 6A:
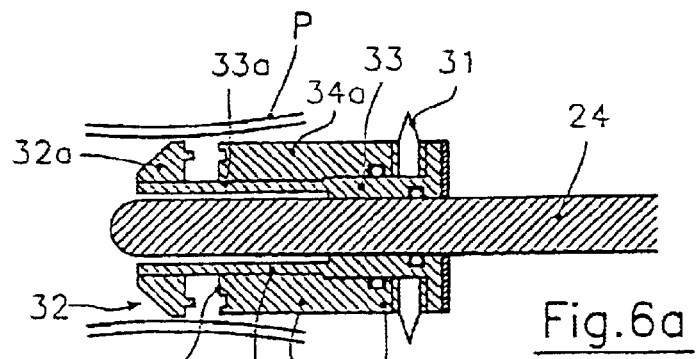
FIGS. 6a, 6b, 6c schematically show the operation of the clamping means integral to the rear end of the endoscopic device of FIG. 3.
Figure 6B:
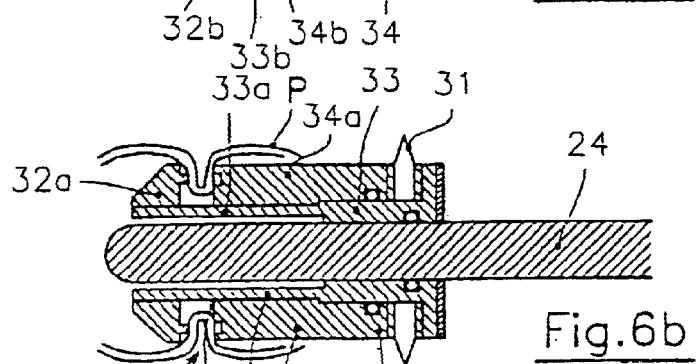
Figure 6C:
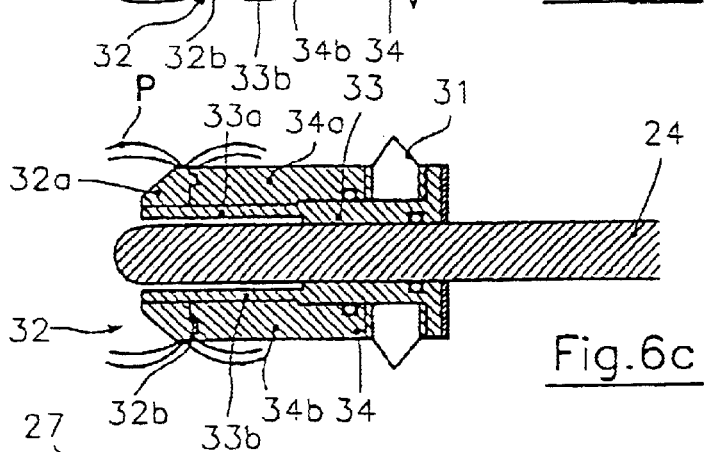

As shown in FIGS. 6*a, b, c*, rear end section 21*c* of the device comprises a first sleeve 33 coaxially mounted on stem 24 and slidable thereon. Sleeve 33 has a flanged end one side of which is fixed to rear flange 22*b* of intermediate section 21*a*, the other one being fixed to a bellow 31 coaxial thereto. A pair of arm 33*a*, 33*b* extend from sleeve 33 in a diametrically opposed and parallel relationship with respect to stem 24. Arms 33*a*, 33*b* are arranged on a plane rotated of an angle of 90° with respect to the two jaw portions of first clamp 27 and support jaws 32*a* and 32*b* of second clamp 32. Likewise first clamp 27, second clamp 32 is formed by two diametrically opposed clamp portions and therefore clamps 27 and 32 are in a substantially crosswise arrangement with respect to the longitudinal axis of the device, as shown in FIG. 4.

In particular, the pair of portions of jaw 32*a* are fixed to the free ends of arms 33*a* and 33*b*, while the pair of portions of mobile jaw 32*b* are formed at the end of two further arms 34*a* and 34*b* extending at the outside of arms 33*a* and 33*b* and parallel thereto from a second sleeve 34 integral to bellow 31 and axially slidable on sleeve 33. The sliding of arms 34*a, b* with respect to arms 33*a, b* is limited at one side by the abutment with fixed jaw 32*a* and at the other side by the mutual abutment between shoulders 35 and 36 formed on the respective sliding surfaces.

Tubular connector 29 houses a plurality of pneumatic tubes communicating to a series of conduits formed in stem 24. In particular, with reference to FIG. 3, conduits 37 and 38 are provided for creating a depression or feeding compressed air between jaws 27*a, b* of first clamp 27 and jaws 32*a, b* of second clamp 32, to help engagement and, respectively, release of the surrounding wall portion P of the body cavity, and conduits 45 and 46 to suck or feed air from/to bellows 31 and 22, thereby causing them to extend and respectively to retract. A conduit for feeding air to head 25 is also provided to blow air against the cavity wall during the forward motion. These conduits are all shown in FIG. 3 for sake of simplicity. Conduits 38 and 45 are helically arranged inside chamber 23.

The operating cycle of the endoscopic device according to the second embodiment of the invention is shown in FIGS. 8*a*–8*g*. First, vacuum is created in correspondence of the jaws of second camp 32 to cause a surrounding wall portion P of the body cavity to collapse therebetween (FIG. 8*a*), then compressed air is entered in bellows 31 which in this way is elongated causing the closure of second clamp 32 and the grasping of wall portion P (FIG. 8*b*). Compressed air is entered in chamber 23 of bellows 22 which expands pushing front head 25 forward. In view of the connection through stem 24 front head 25 pull first clamp 27 forward (FIG. 8*c*) After having created a depression between the jaws of first clamp 27 to make the surrounding wall portion P to collapse therebetween, first clamp 27 is closed by traction of actuating wire 26 to grasp wall portion P (FIG. 8*d*). At this point second clamp 32 can be opened by sucking air from bellow 31, to release the wall portion P held thereby (FIG. 8*e*). Once second clamp 32 is opened, it is made to advance with respect to first clamp 27 by sucking air from bellow 22, which retracts (FIG. 8*f*). In these conditions, after second clamp 32 is held again to the body cavity wall, first clamp 27 is opened and the cycle repeated for a further advancement step.

Opposed grip surfaces of jaws of first and second clamp 27 and 32 are formed with an annular groove and a corresponding step for engaging therewith to improve the grip of the wall portion of the body cavity.

It will be appreciated that in the second embodiment of the invention clamps 27 and 32 alternately overtake each other during each advancement step of the device and the clamp that in turn is in the distal position is the gripping one, while the other one is free and is pulled forward. This prevents the body cavity wall, due to its easily yielding nature, from retracting into folds together with the device in the retraction step and extending in the next extension step without achieving any real forward motion of the device.

From the foregoing it is clear that the endoscopic device according to the invention can migrate through a body cavity of tubular shape apart from the consistency of the walls and the friction that can be afforded by them, because it is able to grasp at the cavity wall before exerting its propulsive push. The increased patient's comfort and the reduction of manual handling made possible with the device of the invention could promote the possibility of mass screening the population for gasto-itnestinal aliments, in particular to carry out colonoscopy and rectosigmoidoscopy, this being a particularly important inspection, in so far as about 70% of the colon cancers are localized in the first tract or the colon. In addition to inspection and diagnosis, future integration of miniaturized endoscopic tools onboard the locomotive device would allow therapeutic procedures to be performed as well.

Several variations may be brought to the above described endoscopic device. Front and rear end sections can be removably connected to the intermediate section so as to be easily replaced in case of damage, for example due to clogging by pollutants, or for maintenance. The wall of the intermediate section can be constituted by an elastically extensible smooth tube instead of a bellows. The device could be made with disposable plastic materials, provided that they are suitable for insertion in a body cavity.

Even if in the present embodiments of the invention pneumatically actuated bellows means have been provided for controlling the extension and the retraction of the intermediate section and the opening and closing of the clamping means, it is clear that, as an alternative, any equivalent linear actuating means such as elastic means or minimotors, can be used. Likewise, compressed air distribution can be carried out in a different way from what has been illustrated, for example by using microvalves within the device, possibly controlled with shape memory alloy actuators.

Further variations and/or modifications can be brought to the endoscopic device according to the present invention, without departing from the scope of the invention as set forth in the attached claims.

What is claimed is:

1. An endoscopic device for locomotion in a body cavity according to a prefixed advancing direction (A) comprising at least a variable length intermediate section (1*a*, 21*a*) extending between a front end section (1*b*, 21*b*) and a rear end section (1*c*, 21*c*) with respect to said direction and characterized in that it further comprises first and second clamping means (7,12,27,32) integral to said front end section and, respectively, said rear section, adapted for alternately grasping respective surrounding portions of wall (P) of said body cavity, and sucking means (13,14,37,38) associated to said first and second clamping means for creating a depression sufficient to cause said body cavity wall portions to collapse within said first and second clamping means while they are in an open condition, means for actuating alternate extensions and retractions of said intermediate section and actuating means (6,11,26,31) of said first and second clamping means being further provided for synchronous operation to generate a forward motion in said prefixed direction of said rear end section due to a retraction of said intermediate section, the wall portion (P) surrounding said first clamping means adapted to be firmly held therebetween, and to generate a forward motion of said front end section in the same direction due to an extension of said intermediate section, the wall portion (P) surrounding said second clamping means adapted to be firmly held therebetween.

2. The endoscopic device according to claim 1, wherein said first (7) and second (12) clamping means are arranged at opposite sides of said variable length intermediate section (1a).

3. The endoscopic device according to claim 1, wherein said first (27) and second (32) clamping means are arranged at the same side of said variable length intermediate section (21).

4. The endoscopic device according to claim 3, wherein said first (27) and second (32) clamping means are arranged in correspondence of rear end section (21c) thereof.

5. The endoscopic device according to any one of claims 3 and 4, wherein said first (27) and second (32) clamping means are arranged on two perpendicular planes and each comprises a pair of jaws being formed each by a pair of diametrical jaw portions.

6. The endoscopic device according to claims 1 or 2, wherein said front/rear end section (1b/1c) comprises a front/rear end head (5/8) and a respective stem (4,10) integral to it, to which a jaw (7b, 12b) of said first/second clamping means (7,12) is fixed, the other jaw (7a, 12a) being slidably mounted on said respective stem (4,10).

7. The endoscopic device according to claim 6, wherein said actuating means of said first clamping means (7) comprise a pneumatically extendable and retractable bellows (6) integral to said slidable jaw (7a) and said intermediate section (1a).

8. The endoscopic device according to claim 6, wherein said actuating means of said second clamping means (12) comprise a pneumatically extendable and retractable bellows (11) integral to said slidable jaw (12a) and said rear head (8), said fixed jaw (12b) being integral to said intermediate section (1a).

9. The endoscopic device according to claims 1 or 3, wherein said front end section (21b) comprises a front head (25) and a stem (24) integral to said head axially extending through said variable length intermediate section (21a) and said rear end section (21c), at the free end of said stem a jaw (27b) of said first clamping means (27) being fixed, the other jaw (27a) being slidably mounted on said stem (24).

10. The endoscopic device according to claim 9, wherein said actuating means of said first clamping means (27) comprise an actuating wire (26) operable from the outside fixed to said slidable jaw (27a).

11. The endoscopic device according to claim 10, wherein said actuating wire (26) is fixed to a bracket (28) axially slidable with respect to said stem (24) and integral to said slidable jaw (37a).

12. The endoscopic device according to claims 1 or 3, wherein said rear end section (21c) comprises a first sleeve (33) integral to said variable length intermediate section (21c), a jaw (32a) of said second clamping means (32) being fixed to the free end thereof, the other jaw (32b) being formed at the end of a second sleeve (34) slidable on said first sleeve (33).

13. The endoscopic device according to claim 12, wherein said actuating means of said second clamping means (32) comprise a bellows (31) for connecting said first and second sleeve (33, 34).

14. The endoscopic device according to claim 12, wherein said first and second sleeve (33,34) each comprises a tubular portion coaxial to said stem (24), respective pair of coplanar and diametrically opposed arms (33a,b; 34a, b) extending from said tubular portion for supporting said fixed jaw (32a) and, respectively, said slidable jaw (32b).

15. The endoscopic device according to claims 1 or 3, wherein said sucking means comprise pneumatic conduits (13,14,37,38) formed within said stem (8,10,24) connected to a outside vacuum and compressed air source (50) and outflowing between the jaws of said clamping means (7,12, 27,32), said outside source being selectively operated to provide compressed air to be blown between said jaws when they open.

16. The endoscopic device according to claims 1 or 3, wherein said intermediate section (1a, 21a) is formed by a flexible and elastic bellows body (2,22) defining a chamber (3,23) and said means for actuating alternate extensions and retractions of said intermediate section (1a, 21a) comprise a pneumatic conduit (40,46) formed in said stem (10,24) and communicating with said chamber (3,23) and said outside vacuum and compressed air source (50) respectively.

17. The endoscopic device according to claim 7, wherein said bellows (6,11,31) communicate through respective pneumatic conduits (41,42,38) with said outside vacuum and compressed air source (50) for selectively feeding compressed air or creating a depression therein to cause their extension or retraction.

18. The endoscopic device according to claims 1 or 3, wherein said front end section (1b, 21b) is provided with means, for blowing compressed air in said body cavity to cause the surrounding wall thereof to spread apart during the forward motion, connected through a pneumatic conduit (43,47) to said outside source (50).

19. The endoscopic device according to claim 8, wherein said bellows (6,11,31) communicate through respective pneumatic conduits (41,42,38) with said outside vacuum and compressed air source (50) for selectively feeding compressed air or creating a depression therein to cause their extension or retraction.

20. Method for the locomotion of an endoscopic device through a body cavity, by means of a succession of extensions and retractions of at least one variable length intermediate section (1a, 21a) in a prefixed direction (A) defining a front end section (1b, 21b) and a rear end section (1c, 21c) of said device, first and second clamping means (7,12,27,32) being associated to said front and, respectively, rear end section, said first and second clamping means being selectively operable from the outside synchronously to said extensions and retractions of said intermediate section, said method being characterized in that a pneumatic depression is selectively induced by suction in correspondence to one of said first (7,27) or second (12,32) clamping means in their open conditions, said depression being such that the surrounding wall portion (P) of said body cavity is caused to collapse within said clamping means, said clamping means being then closed to grasp said surrounding wall portion (P) and firmly hold one respective end section (1*b*, 1*c*, 21*b*, 21*c*) thereto, thereby allowing the free movement of the other end section in the prefixed direction due to extensions and retractions of the intermediate section.

21. The method according to claim 20, comprising a series of advancing cycles, each having the following steps: inducing said pneumatic depression by suction in correspondence to said second clamping means (12,32) in their open condition, thereby causing the surrounding wall portion (P) to collapse therewith; —closing said second clamping means (12,32) to grasp said surrounding wall portion; —extending said variable length intermediate section (1*a*, 21*a*) from a retracted condition to an extended condition; —inducing said pneumatic depression by suction in correspondence to said first clamping means (7,27) in their open conditions to cause the surrounding wall portion (P) to collapse therewith; —closing said first clamping means (7,27) to grasp said surrounding wall portion therewith; —opening said second clamping means (12,32) to release said surrounding wall portion therefrom; —retracting said variable length intermediate section (1*a*, 21*a*) from said extended condition to said retracted condition.

22. Method according to claims 20 or 21, wherein, after each opening step of said clamping means to release said surrounding wall portion, air is radially blown against it to enlarge said body cavity.

23. The method according to claims 20 or 21, wherein the extension or retraction of said variable length intermediate section are performed by adduction or, respectively, suction of a fluid to/from a chamber (3,23) defined in said intermediate section, which is made of a substantially deformable material.

24. The method according to claim 23, wherein said fluid is air.

* * * * *